United States Patent [19]

von Recûm

[11] Patent Number: 4,488,319
[45] Date of Patent: Dec. 18, 1984

[54] METHOD OF TWO-STAGE IMPLANTATION OF A JOINT PROSTHESIS AND PROSTHETIC PRODUCT

[75] Inventor: Andreas F. von Recûm, Clemson, S.C.

[73] Assignee: Clemson University, Clemson, S.C.

[21] Appl. No.: 314,798

[22] Filed: Oct. 26, 1981

[51] Int. Cl.³ ............................................... A61F 1/04
[52] U.S. Cl. ........................................ 3/1.913; 3/1.9;
3/1; 128/92 C; 128/92 CA
[58] Field of Search ........... 128/92 C, 92 CA, 92 BC, 128/92 G; 3/1.9, 1.91, 1.912, 1.913

[56] References Cited

U.S. PATENT DOCUMENTS

| | | | |
|---|---|---|---|
| 2,781,758 | 2/1957 | Chevalier | 3/1.913 |
| 3,605,123 | 9/1971 | Hahn | 3/1.9 |
| 3,806,957 | 4/1974 | Shersher | 128/92 CA |
| 3,896,505 | 7/1975 | Timmermans | 3/1.913 |
| 3,906,550 | 9/1975 | Rostoker et al. | 3/1.913 X |
| 3,918,441 | 11/1975 | Getscher | 128/92 CA X |
| 3,971,134 | 7/1976 | Bokros | 3/1 |
| 4,051,559 | 10/1977 | Pifferi | 3/1.912 |
| 4,115,875 | 9/1978 | Rambert et al. | 3/1.913 |
| 4,164,794 | 8/1979 | Spector et al. | 3/1.913 X |
| 4,202,055 | 5/1980 | Reiner et al. | 3/1.913 X |

FOREIGN PATENT DOCUMENTS 2854334  6/1980  Fed. Rep. of Germany ....... 3/1.913

Primary Examiner—Richard J. Apley
Assistant Examiner—David J. Isabella
Attorney, Agent, or Firm—Wellington M. Manning

[57] ABSTRACT

A two step surgical technique for implantation of a joint prosthesis. A bone cavity adjacent the effected joint is prepared for receipt of a prosthetic stem having porosities therealong for dynamic bony interfacial fixation and a tip adapted for subsequent removable securement to a joint element. The effected joint is resectioned in a subsequent second surgical technique and the opposing joint component is prepared for receipt of a prosthetic joint. The prosthetic joint is then implanted and removably secured to said previously implanted stem. A two piece implantable prosthesis is also disclosed and claimed.

6 Claims, 7 Drawing Figures

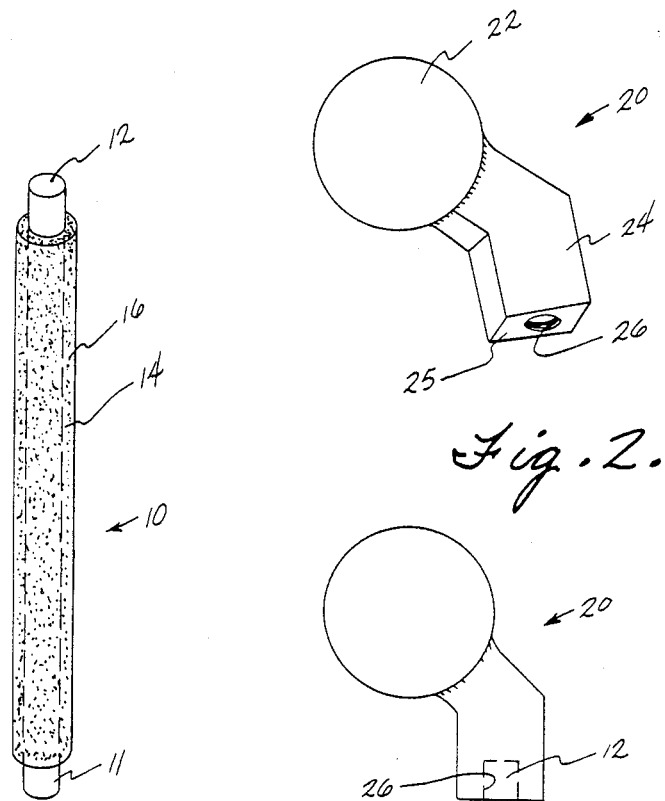
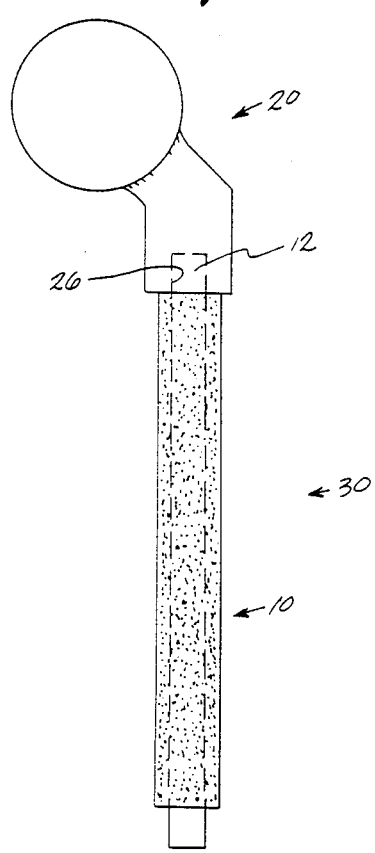
Fig. 1.
Fig. 2.
Fig. 3.

METHOD OF TWO-STAGE IMPLANTATION OF A JOINT PROSTHESIS AND PROSTHETIC PRODUCT

BACKGROUND OF THE INVENTION

The present invention relates to the field of medical prostheses and a two-stage surgical implantation of same to replace a defective joint, such as a hip joint.

Surgical techniques have heretofore existed for the implantation of prosthesis in humans and animals to replace diseased, defective, or damaged portions of the anatomy, such as the various articulating joints of the body. For a number of years medical procedures have been employed for the implantation of a porous prosthesis, after which, bony tissues reforms in porosities of the implant to anchor same within a prepared bone cavity. In similar fashion, prostheses have been surgically implanted utilizing polymeric cement compositions. The cement composition is forced into a prepared bone cavity, after which the prosthesis is properly positioned within the cavity, surrounded by the cement, with the joint component of the prosthesis being properly located in the acetabulum cavity or the like. In situ curing of the cement composition then secures the prosthesis stem within the cavity. A more recent implantation technique has utilized a prosthesis precoated with a cementitious composition similar to the bone cement composition that is to be utilized during the implant procedure. The precoat is cured in vitro to provide a generally pore-free, outer polymer surface which then bonds to the bone cement in situ during implantation to provide improved implant fixation. A significant development effort has also been expended in the area of prosthesis design.

In general, certain problems or disadvantages accompany all current implantation techniques. In particular, prostheses implanted with bone cement are subject to failure after a number of years due to stress fractures across the bone-cement-prosthesis interfaces. Should failure occur, it becomes necessary to remove the prosthesis, and to repeat the procedure, both of which are undesirable to the patient and are quite problematical in success. Tissue ingrowth fixation techniques alluded to above, have heretofore involved a one-step surgical procedure in which the bone canal adjacent a joint is reamed to define an appropriate opening, the bone joint, per se, is resectioned and a one or two-piece prosthesis is surgically implanted. A prolonged postoperative period is necessary to permit bone tissue ingrowth into porosities of the prosthesis before the joint can be utilized or, specifically with regard to the hip joint, before the patient may become ambulatory. Such prolonged patient immobilization is highly undesirable and susceptible to cause disuse muscle atrophy, permanent or temporary reduction of joint function, bone resorption, and general degeneration of patient health. The likelihood of such consequences has generally, negated the employment of bone ingrowth fixation procedures on elderly patients, or other patients where prolonged immobilization would be highly undesirable.

The method and product according to the present invention overcome the disadvantages noted above with respect to prior techniques of implantation, particularly implantation of a prosthetic hip joint. Specifically, after a first surgical technique in which only a stem portion of the prosthesis is implanted, the patient may return to an ambulatory condition very quickly since the joint is not affected. Indirect loading of the stem during normal mobility, accelerates dynamic bony interfacial fixation with the stem, preferably bone ingrowth into porosities in the stem and improves the interfacial strength of same with the stem. After suitable interfacial fixation has occurred, the joint is surgically approached and the joint removed while exposing the tip of the previously implanted stem. Thereafter, a prosthetic joint component is inserted and secured to the implanted stem tip. Upon completion of the second surgical technique and a postoperative recuperative period, the prosthesis may be directly loaded. Consequently, the procedure of the present invention may be practiced on elderly patients. The general consequences of the prior prolonged periods of immobilization are vastly diminished if not alleviated, while increasing the speed of rehabilitation and improving interfacial strength between the prosthesis and the bone.

The prior art is devoid of any teaching or suggestion of the procedure or prosthesis of the present invention. Exemplary of the prior art are:
U.S. Pat. No. 3,708,805,
U.S. Pat. No. 3,864,758,
U.S. Pat. No. 3,924,275,
U.S. Pat. No. 4,051,559,
U.S. Pat. No. 4,187,559,
U.S. Pat. No. Re 28,895,
G.B. Pat. No. 1,334,584
Ger. Pat. No. 2,411,617.

SUMMARY OF THE INVENTION

It is an object of the present invention to provide an improved process for the surgical implantation of a medical prosthesis.

Another object of the present invention is to provide an improved procedure for the surgical implantation of a medical prosthesis for an articulating joint, which procedure involves a two-step surgical technique.

Yet another object of the present invention is to provide an improved process for the surgical implantation of a joint prosthesis with very short recuperative periods.

Still further, another object of the present invention is to provide an improved process for the implantation of medical prostheses having surface porosities for bone tissue ingrowth fixation within a bone cavity, which process avoids prolonged postoperative rehabilitation and thus may be conveniently employed on elderly patients.

Still another object of the present invention is to provide an improved medical prosthesis.

Another object of the present invention is to provide a medical prosthesis that is made up of two separable parts which parts are removably securable against relative rotation.

Yet another object of the present invention is to provide an improved medical prosthesis which is capable of surgical implantation and which thereafter is capable of partial removal in the event of joint failure.

Generally speaking, the process for implantation of a joint prosthesis according to teachings of the present invention comprises the steps of surgically implanting a prosthetic stem in a bone cavity adjacent said joint while avoiding disruption of said joint, said stem being adapted for dynamic bony interfacial fixation along at least a major portion of the length of same and a tip of same being adapted for receipt of a prosthetic joint element; permitting adequate bony fixation for securement of said stem within said bone cavity; and thereafter surgically resectioning said joint and implanting a prosthetic joint element therein while securing said joint element to said previously implanted stem.

More specifically, surgical implantation of a prosthetic stem adjacent a joint is preferably achieved by making direct access into the medullary cavity and reaming same within close tolerance to the size and shape of the prosthetic stem. The joint capsule is initially unaffected, such that during and following postoperative recovery, the patient can continue to utilize the joint and, in fact, indirectly loads the prosthetic stem which stimulates the preferred bone tissue ingrowth into stem porosities to achieve a more rapid and more effective fixation of the stem within the bone cavity. In a preferred embodiment, the implanted stem is straight to permit the direct reaming of the bone cavity, and porosities along the outer stem surface may be provided in a polymer coating or otherwise as discussed hereinafter.

During the second surgical technique, the defective element of the articulating joint is resectioned and a prosthetic joint element substituted therefor. Particularly, the joint is surgically approached, the defective articulating element is removed, an appropriate bony or other bed is prepared for receipt of a prosthetic joint element receiving cup, and the prosthetic joint element is thereafter appropriately implanted. Alternatively the prosthetic joint element may be implanted for articulation with the natural opposite joint element. A neck of the articulating joint element is secured to an uncovered tip of the previously implanted stem in such a fashion that relative rotation therebetween is avoided. In the sense of the hip joint, for example, the articulating element is provided by a ball with an appropriate neck extending outwardly and angularly downwardly for receipt of the exposed tip of the previously implanted stem. In order to ensure against relative rotation, the downwardly extending portion of the neck element may, for example, define a tip receiving opening, which may be noncircular in shape and which mates with a like shaped stem tip. Alternatively different configurations and arrangements may be utilized. The joint section of the joint element should have an appropriate outer surface as dictated by the joint to be replaced and the neck section should properly interface with the bone resection surface and be associable with the stem as mentioned above.

The prosthesis assembly that is the subject matter of the present invention comprises an elongated stem, said stem having porosities along at least a portion of the length of same, said porosities being adequate for receipt of ingrowth of bony tissue for mechanically interlocking same within a bone cavity, a tip of said stem being adapted for association with a prosthesis joint element to removably secure said joint element and said stem and to preclude against relative rotation therebetween; and a separate prosthetic joint element, said joint element including a joint surface section and a neck section, said joint surface section having an outer surface compatable with a joint in which it is to be received and said neck section being capable of interfacing with a bone resection surface adjacent the joint, and a portion of said neck section being adapted for removable securement to said tip of said stem.

More specifically as to the prosthesis, the stem of same is preferably straight and of a size according to the dictates of the bone in which implantation is to occur. The stem basically has two sections that are very important to success of the present invention, namely, a tip or end section that is to be exposed immediately adjacent the defective joint, and a body section which extends along a major axis or length of the stem. The outer surface of the body section of the stem is provided with porosities suitable for receipt of ingrowth of bony tissue which mechanically interlocks the stem within the bone cavity. Such porosities may be provided in a polymer coating around the stem or alternatively, may be provided by various techniques of the prior art, either having been produced in situ during manufacture of the stem or thereafter. The tip or end section of the stem is adapted to mate with a portion of the joint element. A predetermined cross sectioned tip may be provided to mate with an opening in the neck section of the joint component, the tip may define an opening for receipt of a portion of the neck section, or the like, so long as the elements are secured and held against relative rotation. Additionally, if necessary, the components may be secured by a pin, threaded fastening element or the like. The joint element of the prosthesis, as mentioned above, is separate from the stem, and is generally comprised of a joint suface section and a neck section angularly disposed with respect to the joint such that the joint component element may be operatively associated with the previously implanted stem without difficulty. Same or different materials may be employed for manufacture of the joint element and stem element of the prosthesis so long as the particular material utilized for either does not interfere with the intended function of the element.

BRIEF DESCRIPTION OF THE DRAWINGS

FIG. 1 is a side view of a prosthetic stem element according to teachings of the present invention.

FIG. 2 is a side view of a joint element of a prosthesis according to the present invention.

FIG. 3 is a side view of a prosthesis according to teachings of the present invention where the elements of FIGS. 1 and 2 are united to illustrate the prosthesis following the second surgical procedure.

DESCRIPTION OF THE PREFERRED EMBODIMENTS

Figure 5:
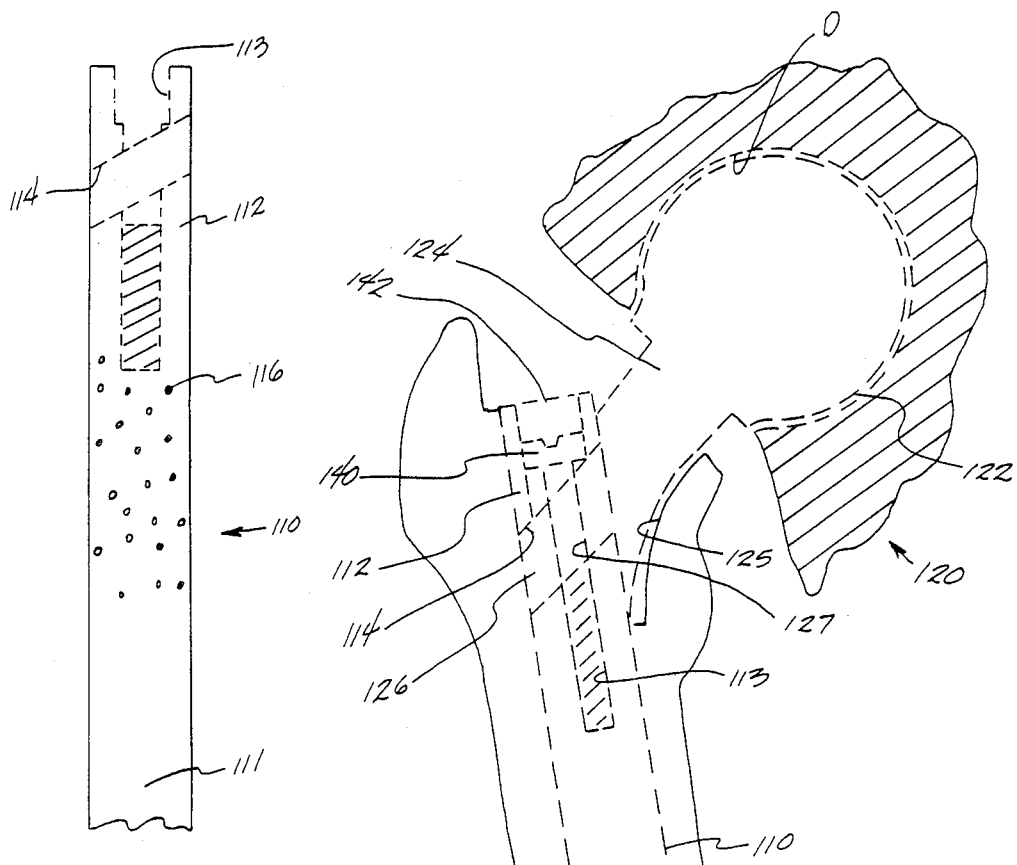
FIG. 5 is an elevation of a further embodiment of a stem element of a prosthesis according to teachings of the present invention.

Making reference to the Figures, preferred embodiments of the present invention will now be described in detail. In FIG. 1, there is shown a prosthetic stem element generally indicated as 10 in the form of a cylindrical rod 11 having a receiving tip section 12 and having a coating 14 along a main body section in which porosities 16 are provided to permit bone tissue ingrowth thereinto. As mentioned hereinbefore, the preferred porosities along the length of the body section of stem 10 may be provided in a surface coating such as a polymethyl methacrylate, polyethylene or the like, may be produced in situ on the metallic surface of the prosthesis by casting, sintering or other methods as illustrated in FIG. 5, or the prosthesis may be treated after manufacture by etching or the like. Such porosities may be produced according to U.S. Pat. No. 3,713,860 in which a prosthesis produced from porous aluminum oxide is impregnated with pure methyl methacrylate monomer. The monomer is polymerized and removed from selected areas to produce the porosities. Likewise U.S. Pat. No. 3,936,887 may be followed in which a prosthesis is produced from vitreous carbon and acrylic polymer, where the vitreous carbon is in the form of microballons which are burst along the outer surface to provide the porosities. Likewise, other techniques may be employed. Metallic prostheses may be fabricated from various materials, for example, cobalt-chromium alloys, titanium alloys, platinum metals, tantalum, stainless steels, and the like, which, either during or after fabrication may be treated to impart porosities or other roughened surface areas that will produce a good mechanical interlock with bone tissue ingrowth.

FIG. 2 illustrates a joint element generally indicated as 20 which comprises a ball section 22 and a neck section 24. Ball section 22 of joint element 20 should be of a particular size and shape to be received within a prosthetic acetabular cup C (See FIG. 4), or a natural acetabulum cavity D (See FIG. 7). When the natural acetabulum of the hip joint is to be resectioned, a proper bony surface is prepared for receipt of a cup C. Ball surface 22 should have a surface characteristic that is compatible with the natural acetabulum, or prosthetic cup as the case may be. A highly polished metallic or a smooth polymeric surface is generally acceptable. When ball surface 22 is properly located in the natural or prosthetic acetabulum, neck section 24 will then extend downwardly and outwardly therefrom to a point where a stem tip receiving opening 26 defined in an outer end 25 of neck 24 will reside over tip 12 of stem 10 (See FIGS. 3 and 4) to properly associate stem 10 and joint element 20. With the joint element 20 interrelated with stem 10, the distal surface 25 of neck section 24 preferably rests in a bony bed L specially prepared in the proximal end of the femur. A close tolerance fit is preferred such that rotational forces applied through the head and neck to the stem are minimized. As mentioned hereinbefore and as specifically set forth in FIG. 4, tip receiving opening 26 is preferably non-circular in shape and intended to receive a like shaped tip 12 therein such that relative rotational movement between joint element 20 and stem 10 is precluded. Obviously, a shaped protrusion may extent from neck 24 and be received within an opening in tip 12. FIG. 3 illustrates an overall prosthesis according to the present invention indicated at 30 with tip receiving opening 26 of joint component 20 residing over tip 12 to associate the two elements.

Figure 6:
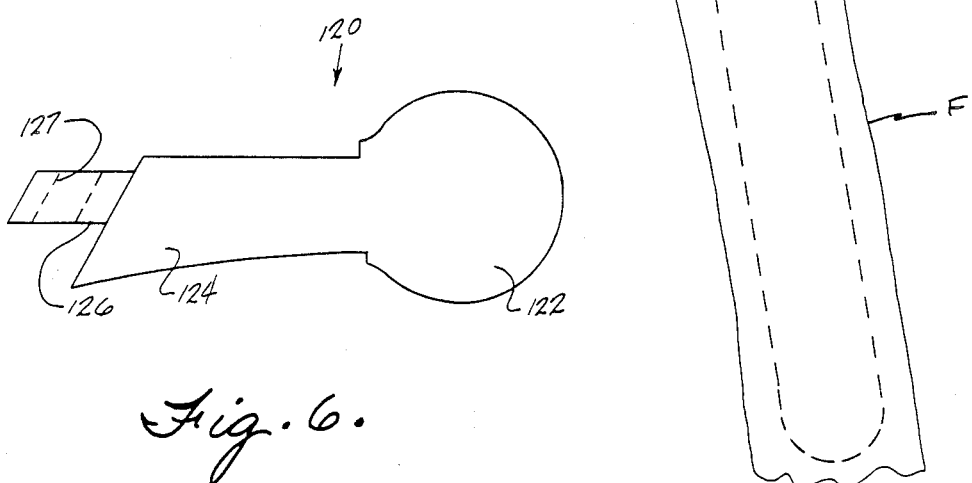
FIG. 6 is a side view of a further prosthetic joint element according to teachings of the present invention, which joint element is associable with the stem illustrated in FIG. 5.
Figure 7:
FIG. 7 is a schematic illustration of a femur showing the prosthesis of FIGS. 5 and 6 in phantom, implanted for articulation with the natural acetabulum.

A further prosthetic embodiment according to teachings of the present invention is illustrated in FIGS. 5 through 7. A straight stem generally 110 is illustrated having porosities 116 in the outer surface of a body section 111 of same, which porosities appear at least along a major portion of the length of stem 110. A tip section 112 of stem 110 defines an opening 113 that extends axially along stem 110 with a further oblique angular opening 114 defined by tip 112 that extends generally transverse with respect to the length of stem 110 and intersects opening 113. A joint component generally 120 is provided having a joint section 122 and a neck section 124. Neck section 124 has a protuberance 126 extending axially outwardly therefrom with protuberance 126 defining an angular opening 127 therethrough. When assembled, protuberance 126 mates with angular opening 114 in stem 110 and angular opening 127 of neck protuberance 126 mates with axial opening 113 of stem 110. A fastening member 140 is threadedly received along axial opening 113, passing through opening 127 to secure joint component 120 to stem 110 (See FIG. 7). Threaded fastening member 140 may extend completely within axial opening 113 with a cover member 142 received atop same to close or plug axial opening 113.

Figure 4:
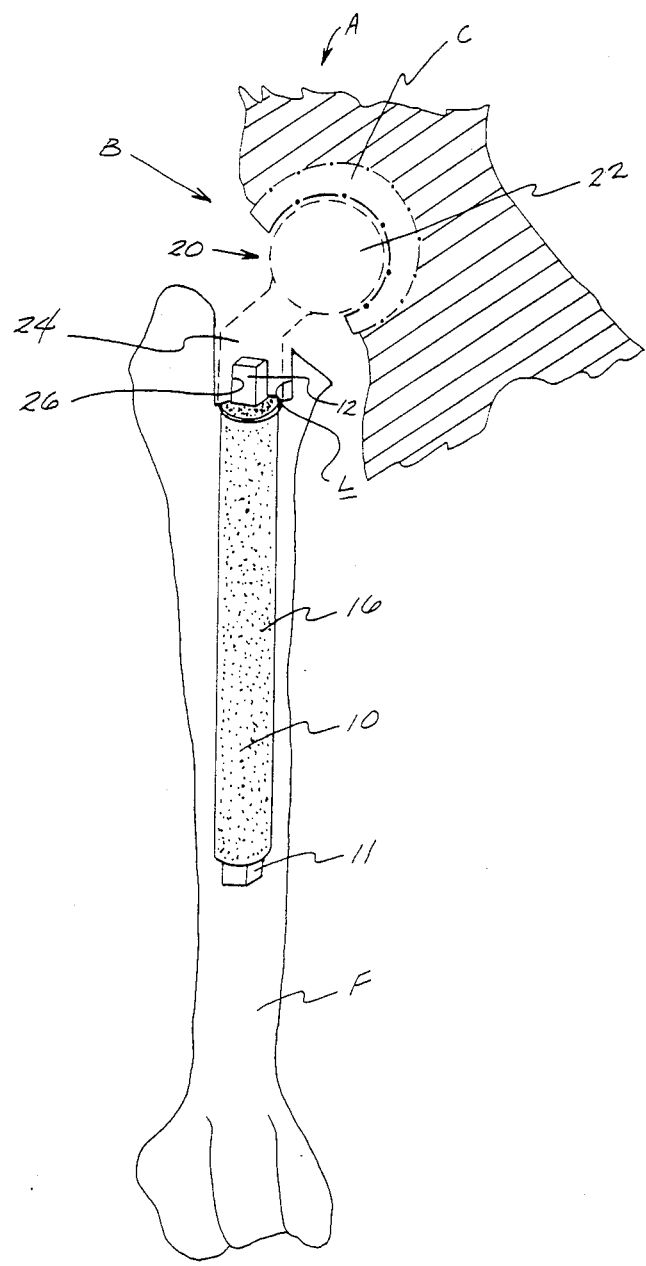
FIG. 4 is a schematic outline of a femur, illustrating a stem according to the teachings of the present invention implanted therein with the tip section exposed and showing a hip joint acetabular cup and and prosthetic joint element in phantom.

In FIG. 7, the embodiment of the prosthesis is illustrated with joint element 120 implanted within a prepared, but natural acetabulum D as opposed to a prosthetic cup as illustrated in FIG. 4. As likewise shown in FIG. 4, a bony bed 125 is prepared in the femur during the second stage of the surgical technique for antirotational receipt and support of section 124 of joint element 120.

With either of the two-piece prostheses illustrated in FIGS. 1 through 7, should the joint component fail, the defective joint component may be replaced without interfering with the implanted stem. A much less complex surgical replacement procedure is thus required, after which the patient may again directly load the prosthesis following post operative recuperation.

The surgical procedure of implantation as mentioned hereinbefore is a two-step surgical technique. The procedure will thus be described with reference to a hip joint, and to the prosthesis embodiment illustrated in FIGS. 1 through 4. It should be understood, however, that the prostheses and techniques according to teachings of the present invention would likewise be suited for other joints of the body, which may normally receive a prosthesis. In FIG. 4, a femur indicated as F is schematically shown which has previously been reamed generally along a line A to provide an opening in the medullary cavity adequate to receive the prosthetic stem 10 therein. In view of the fact that bone tissue ingrowth fixation is achieved an opposed to the use of bone cement or some other technique, it is desirable and preferred that the cavity be reamed as close to the size of the stem as is practical. After appropriate reaming of the femur according to proper surgical techniques, stem 10 is seated therein. Utilizing a straight stem 10, it is possible to ream the cavity in a linear fashion through the fossa intertrochanterica indicated by the line A while avoiding interference with the joint cavity capsule. As illustrated in FIG. 4, the tip 12 of stem 10 is exposed during the second surgical procedure for association with a joint component (illustrated in phantom). In FIG. 4, tip 12 is illustrated in a rectangular configuration, though other configurations would likewise be permissible.

Once stem 10 is implanted, and the surgical technique completed, the patient, after short postoperative recuperation may continue to utilize the affected joint and will accordingly impart indirect loading on stem 10 which stimulates bone tissue ingrowth into the porosities 16 of same, anchoring stem 10 in place. Accordingly, after a matter of a few weeks, prosthetic stem 10 is adequately anchored within the medullary cavity of femur F. A second surgical technique is then accomplished, preferably employing a lateral approach. Particularly an osteotomy of the femoral neck may be performed as indicated by the arrow B, to resection the femoral head. The femoral head and neck are removed, tip 12 of stem 10 is exposed, and a bony bed L is prepared, in the proximal part of femur F around the tip 12 of stem 10 to receive the prosthetic neck 24 (shown in phantom). A prosthetic acetabular cup is then implanted in the acetabulum. During implantation of joint component 20 with cup C, neck section 24 is placed over tip 12 which is received within tip receiving opening 26 to secure the components and to avoid relative rotational movement of joint component 20 with respect to stem 10. Neck 24 generally interfaces with bony bed L. Once joint component 20 is properly positioned, the operative technique may be completed under normal conditions.

Following the second surgical technique as described above, with the stem 10 already firmly anchored in the medullary cavity of femur F, the patient, again after a short postoperative recuperation period may thus return to a mobile status. Direct loading may thus be imparted to the implanted prosthesis.

Dynamic bony interfacial fixation as used herein refers to any arrangement in which at least partial fixation of a stem within a bone cavity is due to mechanical interlock between bone tissue and the surface of the stem, with a continuous reformation of such interface due to bone tissue remodeling. While as mentioned above a porous outer stem surface is preferred for bone tissue ingrowth, obviously an irregular shaped stem surface could also facilitate same, as exemplified, without limitation, by openings through the stem, depressions in the stem and the like.

Having described the present invention in detail, it is obvious that one skilled in the art will be able to make variations and modifications thereto without departing from the scope of the invention. For example, the various embodiments of the prostheses described may be interchanged when desired. Accordingly, the scope of the present invention should be determined only by the claims appended hereto.

That which is claimed is:

1. An improved method for implantation of a joint prosthesis comprising the steps of:
    (a) surgically implanting of prosthetic stem in a bone cavity adjacent said joint while avoiding disruption of said joint, said stem being adapted for dynamic bony interfacial fixation along at least a portion of the length of same, a tip of said stem being adapted for receipt of a prosthetic joint element;
    (b) permitting adequate dynamic bony interfacial fixation between said stem and bony tissue within said bone cavity for securement of said stem; and
    (c) thereafter removing said joint in a second surgical procedure and implanting a prosthetic joint element therefor while securing said joint element to said stem.

2. The method as defined in claim 1 wherein said joint is a hip, and said stem is implanted by obtaining direct access to the medullary cavity, reaming said cavity, and force fitting the stem into said cavity, said stem having a porous outer surface along at least a portion of the length of same.

3. The method as defined in claim 2 wherein after the stem is secured, the joint is approached through a second surgical procedure, the femoral head and neck is removed, and a prosthetic femoral head and neck is implanted, said neck being secured to said stem.

4. The method as defined in claim 3 wherein after removal of the femoral head and neck, a bony bed is prepared in the femur for receipt of the prosthetic neck.

5. The method as defined in claim 4 wherein said neck is secured in said bony bed to preclude transmission of rotational forces from the head and neck through the stem onto the stem bone interface.

6. The method as defined in claim 4 wherein said neck is secured to said stem to preclude against relative rotation of the head and the stem.

* * * * *